US00PP36284P2

(12) United States Plant Patent
Dirr et al.

(10) Patent No.: US PP36,284 P2
(45) Date of Patent: Dec. 3, 2024

(54) ***GARDENIA* PLANT NAMED 'Baildeniaone'**

(50) Latin Name: *Gardenia jasminoides*
Varietal Denomination: Baildeniaone

(71) Applicant: Bailey Nurseries Inc., Newport, MN (US)

(72) Inventors: Michael A. Dirr, Bogart, GA (US); Jeff Beasley, Lavonia, GA (US); Mark Griffith, Watkinsville, GA (US); Rhonda Helvick, Madison, GA (US); Oren McBee, Bishop, GA (US); David Jonathan Roberts, Athens, GA (US); Justin Schulze, Athens, GA (US)

(73) Assignee: BAILEY NURSERIES INC., Newport, MN (US)

( * ) Notice: Subject to any disclaimer, the term of this patent is extended or adjusted under 35 U.S.C. 154(b) by 0 days.

(21) Appl. No.: 18/509,383

(22) Filed: Nov. 15, 2023

(51) Int. Cl.
*A01H 5/02* (2018.01)
*A01H 6/76* (2018.01)

(52) U.S. Cl.
USPC ..... Plt./255
CPC ..... *A01H 6/76* (2018.05)

(58) Field of Classification Search
USPC ..... Plt./255
CPC ..... A01H 6/76; A01H 5/02
See application file for complete search history.

*Primary Examiner* — Keith O. Robinson
(74) *Attorney, Agent, or Firm* — Penny J. Aguirre

(57) ABSTRACT

A new cultivar of *Gardenia* named 'Baildeniaone' that is characterized by its double flowers with a strong fragrance, its uniform and rounded plant habit without pruning, and its good cold tolerance, at least to U.S.D.A. Zone 7.

2 Drawing Sheets

Botanical classification: *Gardenia jasminoides*.
Variety denomination: 'Baildeniaone'.

BACKGROUND OF THE INVENTION

The present invention relates to a new and distinct cultivar of *Gardenia jasminoides*. The new cultivar will be referred to hereafter by its cultivar name, 'Baildeniaone'. 'Baildeniaone' is a new cultivar of *Gardenia* grown for use as a landscape shrub.

The new cultivar was derived from a controlled breeding program conducted by the Inventors in Watkinsville, Georgia. The goal of the breeding program is to develop new cultivars of cape jasmine with good cold winter tolerance.

'Baildeniaone' originated as a seedling that arose from seed planted from open pollination of *Gardenia jasminoides* 'Frostproof' (not patented) in summer of 2008. The male parent is therefore unknown. 'Baildeniaone' was selected as a single unique plant in summer of 2009 from the resulting seedlings.

Asexual propagation of the new cultivar was first accomplished by softwood stem cuttings under the direction of the Inventors in Watkinsville, Georgia in summer of 2010. Asexual propagation by softwood stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Baildeniaone' as a new and unique cultivar of *Gardenia*.

1. 'Baildeniaone' exhibits double flowers with a strong fragrance.

2. 'Baildeniaone' exhibits a uniform and rounded plant habit without pruning.
3. 'Baildeniaone' exhibits good cold tolerance, at least to U.S.D.A. Zone 7.

The female parent differs from 'Baildeniaone' in having a much smaller plant size. 'Baildeniaone' can be most closely compared to the *Gardenia jasminoides* cultivars 'Double Mint' (U.S. Plant Pat. No. 23,507) and 'PIIGA-II' (U.S. Plant Pat. No. 27,258). Both are similar to 'Baildeniaone' in having fragrant double flowers and rounded plant habits. Both differ from 'Baildeniaone' in having smaller plant sizes with lower cold tolerance; sustaining damage at 7° F.

BRIEF DESCRIPTION OF THE DRAWINGS

The accompanying color photographs illustrate the overall appearance and distinct characteristics of the new *Gardenia*. The photograph in FIG. 1 was taken of a 12-year-old plants of the new cultivar as grown in trial garden in Winterville, Georgia. The photographs in FIG. 2 and FIG. 3 were taken of a 1.5-year-old plant as grown outdoors in a 2-gallon container in Yamhill, Oregon.

The photograph in FIG. 1 provides a side view of 'Baildeniaone' in bloom.

Figure 1:
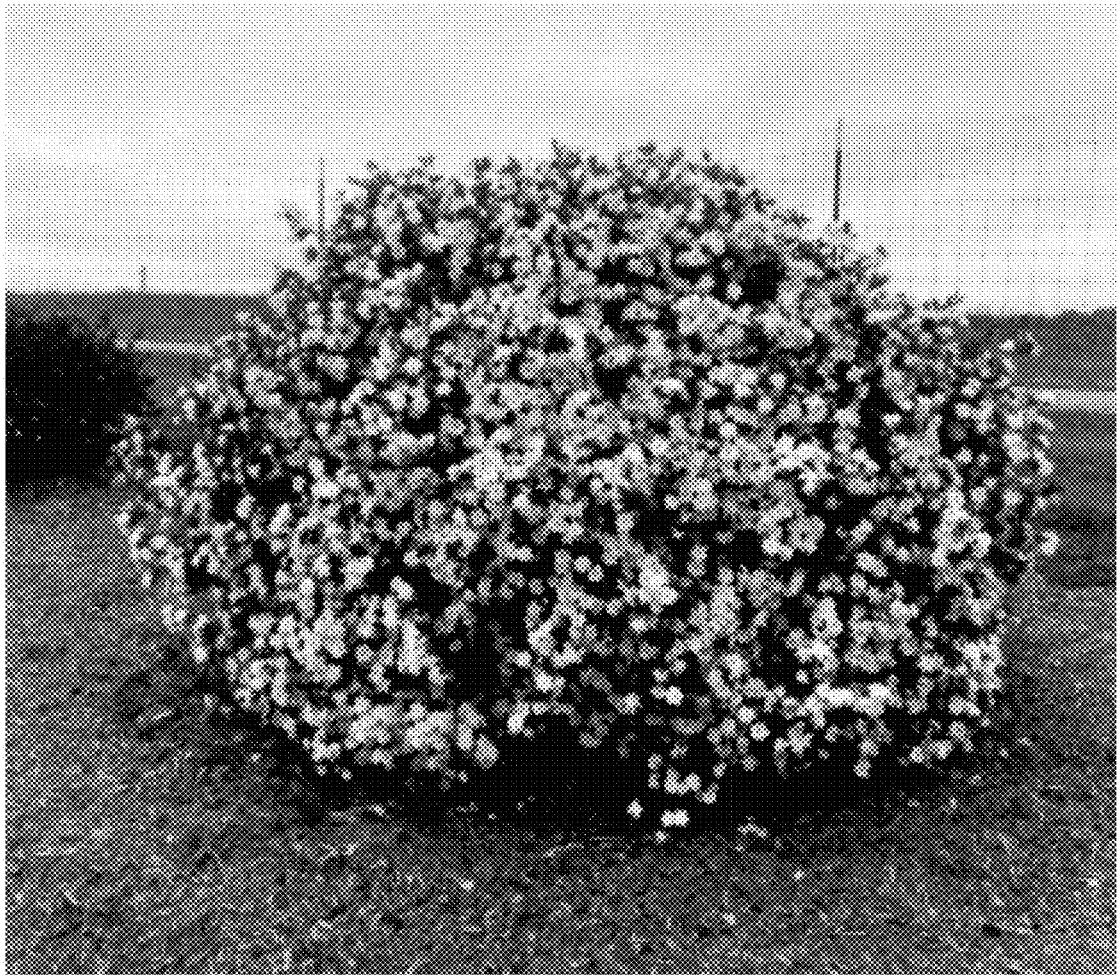
Figure 2:
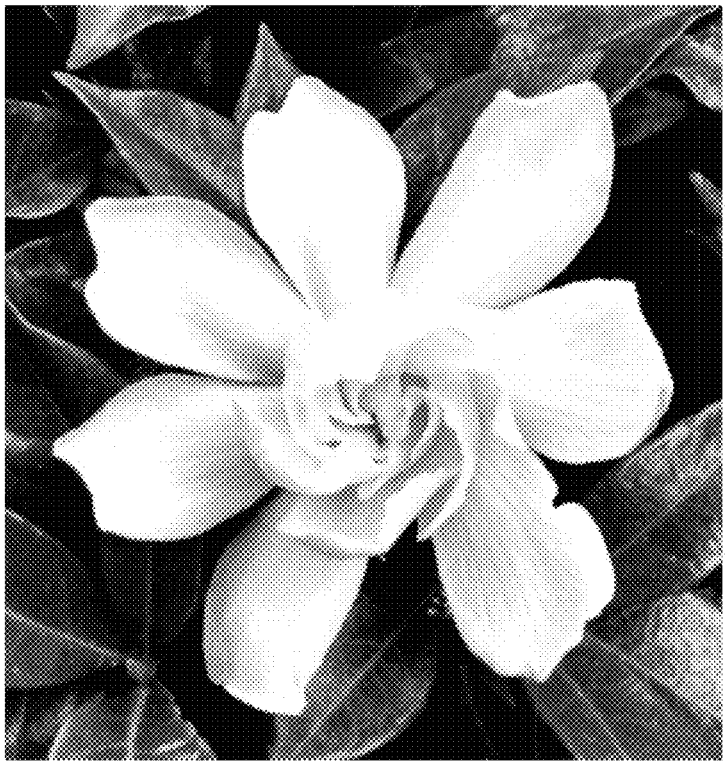

The photograph in FIG. 2 provides a close-up view of a flower of 'Baildeniaone'.

Figure 3:
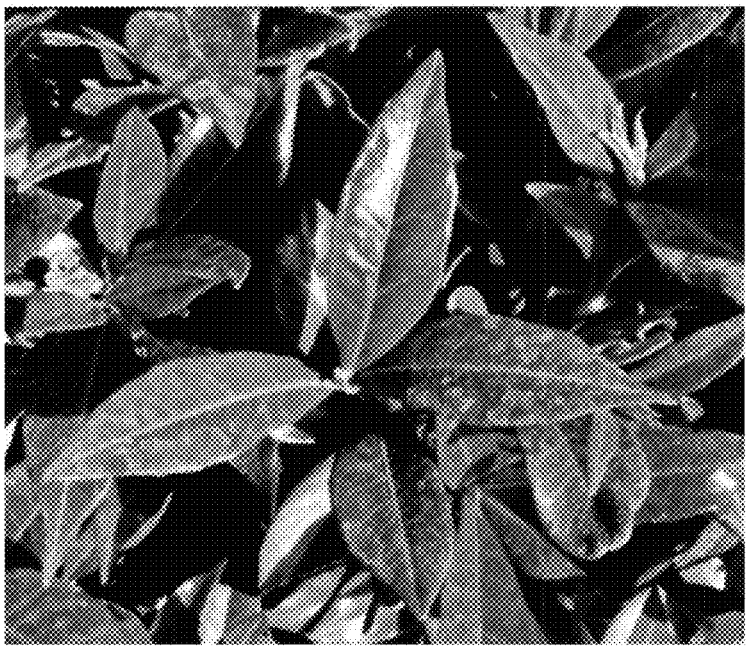

The photograph in FIG. 3 provides a close-up view of the foliage of 'Baildeniaone'.

The colors in the photographs are as close as possible with the photographic and printing technology utilized and the color values cited in the detailed botanical description accurately describe the colors of the new *Gardenia*.

DETAILED BOTANICAL DESCRIPTION

The following is a detailed description of 1.5-year-old plants of the new cultivar as grown in 2-gallon containers outdoors in Yamhill, Oregon. The phenotype of the new cultivar may vary with variations in environmental, climatic, and cultural conditions, as it has not been tested under all possible environmental conditions. The color determination is in accordance with the 2015 Colour Chart of The Royal Horticultural Society, London, England, except where general color terms of ordinary dictionary significance are used.

General description:

*Blooming habit*.—May through June and re-blooming sporadically the rest of the growing season in Yamhill, Oregon.

*Plant type*.—Evergreen shrub.

*Plant habit*.—Compact, mounded, freely branching.

*Height and spread*.—An average of 36 cm in height, 42 cm in width as a 1.5-year-old plant grown in a container, 2.1 m in height in spread as a mature plant in the landscape.

*Cold hardiness*.—At least to U.S.D.A. Zone 7.

*Diseases and pests*.—No susceptibility to resistance to diseases or pests has been observed.

*Propagation*.—Softwood stem cuttings.

*Growth rate*.—Moderately vigorous.

*Root description*.—Fibrous roots, 161A in color.

*Root development*.—Time required for root initiation is 25 days, time required to produce a young plant from a rooted cutting is 60 days.

Branch description:

*Branch color*.—Young; 143B, mature; 143B, covered with bark a blend of 177A and 164A, old wood; 198A, 197A, and 200A.

*Branch quantity*.—Average of 7 main branches, 7 lateral branches per main branch, 4 tertiary branches per lateral branch.

*Branch surface*.—Young; glabrous, glossy, mature; glossy and sometimes covered with young bark, slightly exfoliating and matte, old wood; rugose, matte and sometimes covered with vertical striations.

*Branch shape*.—Round.

*Branch size*.—Main; 5 cm in length, 5 mm in diameter, trunk; 4 cm in diameter, lateral; 21 cm in length, 4 mm in diameter, tertiary; 8 mm in length, 2 mm in diameter.

*Branch strength*.—Strong.

*Internode length*.—Average of 3 cm.

Foliage description:

*Leaf type*.—Simple.

*Leaf attachment*.—Sessile.

*Leaf shape*.—Lanceolate.

*Leaf apex*.—Acuminate.

*Leaf base*.—Cuneate.

*Leaf size*.—Average of 10 cm in length, 3 cm in width.

*Leaf arrangement*.—Opposite, whorled.

*Leaf margin*.—Entire, very slightly undulate.

*Leaf venation*.—Pinnate, upper and lower surface 145A in color.

*Leaf color*.—Young upper surface; 144A, young lower surface; 147C, mature upper surface; NN137A, mature lower surface; 144A.

*Leaf number*.—An average of 25 per branch.

*Leaf surface*.—Upper and lower surface glabrous and glossy.

*Leaf substance*.—Moderately thick.

*Vegetative buds*.—Opposite arrangement, conical in shape, single-scaled, 1.5 cm in length and 4 mm in width, 144A in color.

Inflorescence description:

*Inflorescence type*.—Solitary from upper leaf axils.

*Flower number*.—An average of 20 per plant.

*Flower fragrance*.—Strong, pleasant fragrance typical of *Gardenia*.

*Flower longevity*.—An average of 5 to 7 days, depending on temperature.

*Flower type*.—Salviform with double rotate lobes (rose-like appearance).

*Flower size*.—An average of 9 cm in diameter and 6 cm in depth.

*Flower buds*.—Average of 80 per plant, oblong and conical in shape, held in an upright to slightly drooping angle, an average of 3 cm in length and 1.5 cm in width, surface is glabrous, glossy, color; young buds 143C, before burst 144A and 145A.

*Corolla lobes*.—20 per flower, an average of 3 cm in length and 2 cm in width, 75% overlapping in a whorl, obovate to slightly widely obovate in shape, rounded apex, margins at base to mid-section are entire, mid-section to top undulate and cupped inwards, base is fused into the corolla tube, both surfaces are satiny, glabrous, and matte, moderately thick, color: upper and lower surface when opening and fully open; NN155C, lower surface of outer petals have a stripe on the side; a blend of N144A and N144C.

*Corolla tube*.—An average of 3 cm in length and 5 mm in width, glossy, smooth, satiny surface, color 145C.

*Calyx*.—An average of 2.5 cm in length and 7 mm in diameter, glabrous, glossy, thick, star shaped, 144A to 144B in color.

*Sepals*.—An average of 6, 45% fused to calyx, star shaped en masse, both sides of sepal fused together to appear flattened in shape, pointed apex, glabrous and glossy surface, up to 2.2 cm in length and 2 mm in width, 144A to 144B in color.

*Peduncles*.—Oval in shape, an average of 1 cm in length and 3 mm in diameter, glossy and glabrous surface, 146A in color.

Reproductive organs:

*Gynoecium*.—1 pistil, stigma is prominent, 3-pronged, 8B in color, style; an average of 3 cm in length and 1 mm in diameter, NN155C in color, ovary; 3 mm in diameter, oblong in shape, 161D in color, produces a moderate amount of clear nectar.

*Androecium*.—Up to 5 stamens, filaments are adnate to inner corolla, an average of 1 cm in length, 1 mm in diameter, 165A and 160A in color, anthers; not distinguishable, pollen is abundant in quantity and 12A in color.

*Fruit and seed*.—None observed.

It is claimed:

1. A new and distinct cultivar of *Gardenia* plant named 'Baildeniaone' as herein illustrated and described.

* * * * *